United States Patent
Itano et al.

(10) Patent No.: US 10,485,228 B2
(45) Date of Patent: Nov. 26, 2019

(54) INSECT PEST CONTROL PRODUCT AND INSECT PEST CONTROL METHOD

(71) Applicant: DAINIHON JOCHUGIKU Co., Ltd., Osaka (JP)

(72) Inventors: Taisuke Itano, Osaka (JP); Hiroshi Asai, Osaka (JP); Koji Nakayama, Osaka (JP)

(73) Assignee: DAINIHON JOCHUGIKU Co., Ltd., Osaka (JP)

( * ) Notice: Subject to any disclaimer, the term of this patent is extended or adjusted under 35 U.S.C. 154(b) by 305 days.

(21) Appl. No.: 15/563,274

(22) PCT Filed: Apr. 11, 2016

(86) PCT No.: PCT/JP2016/061670
§ 371 (c)(1),
(2) Date: Sep. 29, 2017

(87) PCT Pub. No.: WO2016/167209
PCT Pub. Date: Oct. 20, 2016

(65) Prior Publication Data
US 2018/0070576 A1    Mar. 15, 2018

(30) Foreign Application Priority Data

Apr. 14, 2015  (JP) ................. 2015-082119

(51) Int. Cl.
*A01N 25/18* (2006.01)
*A01M 1/20* (2006.01)
*A01N 53/00* (2006.01)

(52) U.S. Cl.
CPC ............ *A01M 1/2077* (2013.01); *A01M 1/20* (2013.01); *A01N 25/18* (2013.01); *A01N 53/00* (2013.01); *A01M 2200/012* (2013.01)

(58) Field of Classification Search
CPC .................. A01M 1/2077; A01M 1/20; A01M 2200/012; A01N 25/18; A01N 53/00
See application file for complete search history.

(56) References Cited

U.S. PATENT DOCUMENTS 6,171,608 B1    1/2001    Schmitt et al.

FOREIGN PATENT DOCUMENTS

| AU | 2012200592 | 2/2012 |
|---|---|---|
| CN | 1042042 | 5/1990 |
| EP | 0366226 | 5/1990 |
| JP | 774130 | 8/1995 |
| JP | 7100641 | 11/1995 |
| JP | 08-310907 A | 11/1996 |
| JP | 2000-103712 A | 4/2000 |
| JP | 2000103704 | 4/2000 |
| JP | 2002000158 | 1/2002 |
| JP | 200381720 | 3/2003 |
| JP | 2005095107 | 4/2005 |
| JP | 2009-232915 A | 10/2009 |
| JP | 2015-096541 A | 5/2015 |
| KR | 10-2010-0084958 | 7/2010 |

OTHER PUBLICATIONS

First Office Action issued to corresponding Japanese Application No. 2017-512519 dated Jul. 3, 2018 and its English translation.
Office Action for Taiwanese Patent Application No. 105111267 dated Feb. 16, 2017 along with the English translation.
PCT/JP2016/061670; PCT International Search Report of the International Searching Authority dated Jun. 16, 2016 and its English translation.
The First Examination Report issued to the corresponding Australian Patent Application No. 2016248706 dated Oct. 18, 2018.
The First Office Action issued to the corresponding Korean Patent Application No. 10-2017-7025479 dated Oct. 19, 2018 and its English translation.
Extended European Search Report issued to the corresponding European Patent Application No. 16780000.2 dated Nov. 15, 2018.
Decision of Refusal issued to the corresponding Korean Patent Application No. 10-2017-7025479 dated Mar. 14, 2019 and its English translation.
Decision of Refusal issued to the corresponding Korean Patent Application No. 10-2017-7025479 dated May 7, 2019 and its English translation.

(Continued)

*Primary Examiner* — Ali Soroush
(74) *Attorney, Agent, or Firm* — Renner, Otto, Boisselle & Sklar, LLP

(57) ABSTRACT

An insect pest control product applicable to a water-based insecticidal composition with stable performance over a long time, which comprises a thermal vaporization/diffusion absorbent wick for vaporizing and diffusing a water-based insecticidal composition containing a pyrethroid insecticidal component having a vapor pressure of $2\times10^{-4}$ to $1\times10^{-2}$ mmHg at 30° C., a glycol ether compound having a boiling point of 150-300° C., and water. The wick has a water/oil-based liquid absorption ratio ($V_1/V_2$) within the range of 0.55-1.0, calculated from a speed ($V_1$) at which a water-based liquid formulation rises through the wick, and a speed ($V_2$) at which an oil-based liquid formulation rises through the wick, the water-based liquid formulation contains 40 mass % of diethylene glycol monobutyl ether, and the oil-based liquid formulation is a fluid paraffin having 14 carbon atoms.

17 Claims, No Drawings

(56) References Cited

OTHER PUBLICATIONS

The First Examination Report issued to the corresponding Indian Patent Application No. 201727038010 dated May 15, 2019 and its English translation.
The Second Office Action issued to the corresponding Japanese Patent Application No. 2017-512519 dated Dec. 4, 2018 and its English translation.

INSECT PEST CONTROL PRODUCT AND INSECT PEST CONTROL METHOD

The present application is a U.S. National Stage Application based on and claiming benefit of and priority under 35 U.S.C. § 371 to International Application No. PCT/JP2016/061670, filed 11 Apr. 2016, which in turn claims benefit of and priority to Japanese Application No. 2015-082119, filed 14 Apr. 2015, the entirety of each of which is hereby incorporated herein by reference.

TECHNICAL FIELD

The present invention relates to an insect pest control product comprising a thermal vaporization/diffusion absorbent wick for use in vaporization and diffusion of a water-based insecticidal composition containing a pyrethroid insecticidal component having a relatively high vapor pressure, and an insect pest control method of using the insect pest control product.

BACKGROUND ART

Among insect pest control products for controlling flying insect pests such as mosquitoes and the like are so-called "liquid mosquito killers," which are commercially available. Liquid mosquito killers utilize the technique of putting an absorbent wick in a chemical liquid containing an insecticidal component, allowing the chemical liquid to be absorbed and transported to the top portion of the absorbent wick, and heating the absorbent wick so that the insecticidal component is vaporized and diffused into the atmosphere. Chemical liquids for use in liquid mosquito killers are roughly divided into kerosene-based formulations (referred to as "oil-based formulations") and water-based formulations. Most of the conventional liquid mosquito killers include an oil-based formulation. However, water-based formulations may have advantages over oil-based formulations in terms of usefulness and effectiveness. For example, Patent Document 1 and Patent Document 2 indicate that water-based formulations of insecticide may have a lower risk of catching fire and be more effective in killing insect pests, compared to oil-based formulations of insecticide.

Typical insecticidal components for liquid mosquito killers are pyrethroid compounds. Of pyrethroid compounds, insecticidal components such as allethrin, prallethrin, furamethrin, and the like have been most commonly used, but lately there has been a trend towards using newer insecticidal components such as transfluthrin, metofluthrin, and the like, which have a higher insecticidal activity.

Transfluthrin, metofluthrin, and the like have high vapor pressure and different physical properties, compared to allethrin, prallethrin, and the like. Nevertheless, if an oil-based formulation of transfluthrin, metofluthrin, or the like is used in a liquid mosquito killer, then when an absorbent wick adapted to conventional pyrethroid compounds is directly used, a very significant problem does not arise. Meanwhile, if a water-based formulation of transfluthrin, metofluthrin, or the like is prepared, then when an absorbent wick for conventional pyrethroid compounds is used, the affinity of the water-based formulation for the absorbent wick may be unbalanced, so that the amount of the insecticidal component that is vaporized and diffused may become unstable, and therefore, the insect killing efficacy may be impaired, for example.

In order to solve these problems, the following measures may be taken: (1) improving a chemical liquid formulation; (2) modifying specifications of an absorbent wick; (3) changing or adjusting the temperature of a heat generator; and the like. Measure (3) (changing or adjusting the temperature of a heat generator) is not very practical, because conventional devices used as "liquid mosquito killers" have already been widespread on the market.

As to measure (1) (improving a chemical liquid formulation), Patent Document 3 discloses a mixture of a pyrethroid insecticidal component and a solvent having a high boiling point. Patent Document 3 discloses the formulation of an insect pest control liquid to be thermally vaporized and diffused, that contains metofluthrin and Thio tech (a mixture of paraffin and a naphthene hydrocarbon at a ratio of approximately 6:4). However, Thio tech is not soluble in water, and therefore, such a liquid formulation is, of course, not applicable to water-based liquid mosquito killers.

As to measure (2) (modifying specifications of an absorbent wick), Patent Document 4 discloses a baked molded article that contains aggregate including phosphorus oxide. Patent Document 4 discloses an absorbent wick having a specific surface area of 1.0-3.0 $m^2/g$, a liquid absorption ratio of 15-35%, and a liquid absorption speed of 10-25 mm/h, and indicates that the absorbent wick having these properties is applicable to water-based formulations of chemical liquids.

CITATION LIST

Patent Literature

Patent Document 1: Japanese Examined Patent Application Publication No. H07-74130

Patent Document 2: Japanese Examined Patent Application Publication No. H07-100641

Patent Document 3: Japanese Unexamined Patent Application Publication No. 2003-81720

Patent Document 4: Japanese Unexamined Patent Application Publication No. 2000-103704

SUMMARY OF INVENTION

Technical Problem

In order to stably vaporize and diffuse a chemical liquid into the air in a manner such that the insect pest repellent effect is sustained, it is important to maintain an appropriate balance between the components of the chemical liquid during the vaporization and diffusion. In particular, if a water-based formulation of the chemical liquid is used, it is necessary to vaporize and diffuse an insecticidal component, a surfactant, and water while maintaining a balance between these three components. To this end, it is necessary to well understand the behavior of the chemical liquid in the absorbent wick in addition to the composition of the chemical liquid.

In this regard, in the techniques disclosed in Patent Document 1 and Patent Document 2, attention is focused on a surfactant that is one of the components of the chemical liquid, and the relationship between the volatility of the chemical liquid and the physical properties of the absorbent wick is not taken into consideration. The technique disclosed in Patent Document 3 is for stabilizing the vaporization and diffusion of the chemical liquid over a long period of time by adding a solvent having a high boiling point. In the technique disclosed in Patent Document 3, a commonly used porous material is merely used for the absorbent wick, and there is room for improvement. The technique disclosed in Patent Document 4 is based on a study of the physical properties of the absorbent wick. In fact, this technique is intended to be applied to dl·d-T80-allethrin, bioallethrin, d·d-T80-prallethrin, and the like, which are used in oil-based formulations, and is not intended to be applied to pyrethroid insecticidal components such as transfluthrin, metofluthrin, and the like, which have physical properties different from those of the conventional pyrethroid insecticidal components.

In order to develop a water-based liquid mosquito killer using a water-based insecticidal composition containing three components, i.e. a pyrethroid insecticidal component such as transfluthrin, metofluthrin, or the like, a surfactant, and water, it is necessary to study not only the formulation of the insecticidal composition, but also the behavior of the insecticidal composition in the absorbent wick. In the background art, the latter aspect has not been sufficiently studied.

With the above problems in mind, the present invention has been made. It is an object of the present invention to focus attention on the behavior of a chemical liquid in a thermal vaporization/diffusion absorbent wick, and provide an insect pest control product comprising a thermal vaporization/diffusion absorbent wick that can be used to vaporize and diffuse a chemical liquid containing a pyrethroid insecticidal component having a relatively high vapor pressure, the product being capable of continuing to exert stable performance over a long period of time and applicable to a water-based insecticidal composition. It is another object of the present invention to provide an insect pest control method of using such an insect pest control product.

Solution to Problem

To achieve the object, the present invention provides an insect pest control product comprising a thermal vaporization/diffusion absorbent wick for vaporizing and diffusing a water-based insecticidal composition containing a pyrethroid insecticidal component having a vapor pressure of $2 \times 10^{-4}$ to $1 \times 10^{-2}$ mmHg at 30° C., a glycol ether compound having a boiling point of 150-300° C., and water, wherein the thermal vaporization/diffusion absorbent wick has a water/oil-based liquid absorption ratio $(V_1/V_2)$ within the range of 0.55-1.0, where the water/oil-based liquid absorption ratio $(V_1/V_2)$ is calculated from a speed $(V_1)$ at which a water-based liquid formulation rises through the thermal vaporization/diffusion absorbent wick when a lower portion of the thermal vaporization/diffusion absorbent wick is immersed in the water-based liquid formulation, and a speed $(V_2)$ at which an oil-based liquid formulation rises through the thermal vaporization/diffusion absorbent wick when a lower portion of the thermal vaporization/diffusion absorbent wick is immersed in the oil-based liquid formulation, where the water-based liquid formulation is an aqueous solution containing 40 mass % of diethylene glycol monobutyl ether, and the oil-based liquid formulation is a fluid paraffin having 14 carbon atoms.

In the insect pest control product of the present invention, the water/oil-based liquid absorption ratio $(V_1/V_2)$ is preferably within the range of 0.60-0.85.

In the insect pest control product of the present invention, the pyrethroid insecticidal component is preferably at least one selected from the group consisting of transfluthrin, metofluthrin, and profluthrin.

In the insect pest control product of the present invention, the thermal vaporization/diffusion absorbent wick is preferably a baked wick or a braided wick. When the thermal vaporization/diffusion absorbent wick is a baked wick, the baked wick preferably contains, as raw materials, an inorganic powder, an inorganic binder, and an organic substance. When the thermal vaporization/diffusion absorbent wick is a braided wick, the braided wick preferably has a core member, and a sheath material covering an outer peripheral surface of the core member, and the sheath material preferably contains at least one fiber selected from the group consisting of natural fibers, synthetic fibers, and inorganic fibers.

According to the insect pest control product having any of the above features, the water-based insecticidal composition contains the suitable components, and the thermal vaporization/diffusion absorbent wick has the suitable structure, and the suitable water/oil-based liquid absorption ratio $(V_1/V_2)$. Therefore, when the water-based insecticidal composition is vaporized and diffused from the thermal vaporization/diffusion absorbent wick, stable vaporization and diffusion performance and high insect killing efficacy can be simultaneously achieved over a long period of time.

To achieve the object, the present invention provides an insect pest control method of using the insect pest control product having any of the above features, comprising:

putting the thermal vaporization/diffusion absorbent wick in the water-based insecticidal composition so that the water-based insecticidal composition is absorbed and transported to a top portion of the thermal vaporization/diffusion absorbent wick, and heating the top portion at 60-130° C. so that the pyrethroid insecticidal component is vaporized and diffused into the atmosphere.

According to the insect pest control method having the above feature, the water-based insecticidal composition is thermally vaporized and diffused using the insect pest control product of the present invention, and therefore, stable vaporization and diffusion performance and high insect killing efficacy can be simultaneously achieved over a long period of time.

DESCRIPTION OF EMBODIMENTS

An insect pest control product and insect pest control method according to the present invention will now be described. Note that the present invention is not intended to be limited to embodiments or examples described below.

A water-based insecticidal composition for a liquid mosquito killer (hereinafter simply referred to as a "water-based insecticidal composition") applicable to the insect pest control product of the present invention contains a pyrethroid insecticidal component having a vapor pressure of $2 \times 10^{-4}$ to $1 \times 10^{-2}$ mmHg at 30° C. Examples of such a pyrethroid insecticidal component include transfluthrin, metofluthrin, profluthrin, empenthrin, terallethrin, 4-methoxymethyl-2,3,5,6-tetrafluorobenzyl-chrysanthemate, 4-methoxymethyl-2,3,5,6-tetrafluorobenzyl-2,2-dimethyl-3-(2-chloro-2-trifluoromethylvinyl)cyclopropane carboxylate, and the like. Of them, transfluthrin, metofluthrin, and profluthrin are preferable, more preferably transfluthrin, in terms of thermal vaporization and diffusion capability, insect killing efficacy, stability, etc. The above pyrethroid insecticidal components may be used alone or in combination. If there are optical or geometrical isomers based on asymmetric carbon for the acid moiety or alcohol moiety of the pyrethroid insecticidal component, these pyrethroid insecticidal component isomers can be used in the present invention.

The content of the pyrethroid insecticidal component in the water-based insecticidal composition is preferably 0.1-3.0 mass %. If the content is less than 0.1 mass %, sufficient insect killing efficacy may not be achieved. Meanwhile, if the content is more than 3.0 mass %, the properties of the water-based insecticidal composition may be impaired.

The water-based insecticidal composition is prepared as a water-based liquid formulation. Therefore, water is used as the solvent for the water-based insecticidal composition. The water-based liquid formulation has a lower risk of catching fire and is easily made more effective in killing insect pests, compared to the oil-based liquid formulation. The water-based liquid formulation is prepared by mixing water with the pyrethroid insecticidal component and a glycol ether compound having a boiling point of 150-300° C., preferably 200-260° C. The glycol ether compound has the following actions: (1) solubilizing the pyrethroid insecticidal component; (2) improving the thermal vaporization and diffusion capability; and (3) mediating between the pyrethroid insecticidal component and water so that the three components are thermally vaporized and diffused while the ratio of the three components is maintained constant. Furthermore, it is recognized that the glycol ether compound acts as an "efficacy enhancer" for pyrethroid-susceptible insect pests, and has the effect of suppressing the decrease of the insect killing efficacy for insect pests having reduced susceptibility.

The content of the glycol ether compound in the water-based insecticidal composition is preferably 10-70 mass %. If the content is less than 10 mass %, not only is it difficult to prepare a water-based formulation of the water-based insecticidal composition, but also the action of the water-based insecticidal composition as an efficacy enhancer, and the effect of suppressing the decrease of the insect killing efficacy, are poor. Meanwhile, if the content is more than 70 mass %, not only is the insect killing efficacy no longer enhanced, but also the risk of catching fire increases, and therefore, the advantage of being a water-based formulation is likely to be impaired.

Examples of the glycol ether compound include diethylene glycol monoethyl ether (boiling point: 202° C.), diethylene glycol monoisopropyl ether (boiling point: 207° C., hereinafter referred to as "DEMIP"), diethylene glycol monobutyl ether (boiling point: 231° C., hereinafter referred to as "DEMB"), diethylene glycol monoisobutyl ether (boiling point: 220° C., hereinafter referred to as "DEMIB"), diethylene glycol monohexyl ether (boiling point: 259° C., hereinafter referred to as "DEMH"), diethylene glycol mono2-ethylhexyl ether (boiling point: 272° C.), diethylene glycol monophenyl ether (boiling point: 283° C.), triethylene glycol monomethyl ether (boiling point: 249° C.), propylene glycol mono-tertiary butyl ether (boiling point: 151° C.), dipropylene glycol monomethyl ether (boiling point: 188° C.), dipropylene glycol monopropyl ether (boiling point: 210° C., hereinafter referred to as "DPMP"), 3-methoxy-1,2-propanediol (boiling point: 220° C.), and the like. Of them, diethylene glycol monoethyl ether, diethylene glycol monoisopropyl ether, diethylene glycol monobutyl ether, diethylene glycol monoisobutyl ether, and diethylene glycol monohexyl ether are preferable, more preferably diethylene glycol monobutyl ether. The above glycol ether compounds may be used alone or in combination.

Other various components may be added to the water-based insecticidal composition. For example, repellent components such as DEET, terpene compounds, natural essential oils, and aroma chemicals, antibacterial agents, antifungal agents, stabilizers such as dibutylhydroxytoluene (BHT), methyl parahydroxybenzoate, and the like, pH adjusting agents, coloring agents, deodorants such as tea extracts, tea leaf dry distilled solutions, and the like may be added as appropriate. During the preparation of the water-based insecticidal composition, lower alcohols such as ethanol, isopropanol, and the like, ester or ether solvents, kerosene, solubilizers, and dispersants may be used, as appropriate, in an amount that does not impair the advantage of being a water-based formulation, in addition to water. The water-based insecticidal composition thus prepared is placed in a container body (not shown) comprising a thermal vaporization/diffusion absorbent wick, so that the insect pest control product (water-based liquid mosquito killer) of the present invention is constructed.

In the insect pest control product of the present invention, the thermal vaporization/diffusion absorbent wick has a water/oil-based liquid absorption ratio $(V_1/V_2)$ that falls within a suitable range. As used herein, the term "water/oil-based liquid absorption ratio $(V_1/V_2)$" with respect to a thermal vaporization/diffusion absorbent wick refers to a parameter related to the vaporization and diffusion capability of a chemical agent from the absorbent wick, which is specified as followed. Initially, an aqueous solution containing 40 mass % of diethylene glycol monobutyl ether, and a fluid paraffin having 14 carbon atoms, are prepared as a water-based liquid formulation and an oil-based liquid formulation, respectively. Next, the water-based liquid formulation and the oil-based liquid formulation are poured into respective suitable containers to a height of 15 mm, and a thermal vaporization/diffusion absorbent wick having a full length of approximately 70 mm is placed in an upright position on the bottom surface of each container so that a lower portion of the thermal vaporization/diffusion absorbent wick is immersed in each liquid formulation. These containers are allowed to stand for a predetermined period of time. The distance (mm) by which each liquid formulation is absorbed and rises through the thermal vaporization/diffusion absorbent wick (referred to as a "rise distance") is measured. Such a distance (mm) is measured within the height range of 20-60 mm of the thermal vaporization/diffusion absorbent wick at three or more points in time. For the measurement of the rise distance at which a liquid formulation reaches in the thermal vaporization/diffusion absorbent wick, the height range of approximately 25-60 mm of the thermal vaporization/diffusion absorbent wick is easily observed, and the liquid absorption speed is stable within the height range. Therefore, at least three points in time may be set such that the rise distance falls within the range, according to materials for the thermal vaporization/diffusion absorbent wick. For example, at least three measurement points are suitably set within the range of approximately 3-15 hours when the thermal vaporization/diffusion absorbent wick is a baked wick produced by baking a mixture of an inorganic powder with an organic substance and an inorganic binder at 600-2000° C., and within the range of approximately 5-15 min when the thermal vaporization/diffusion absorbent wick is a braided wick obtained by covering the outer peripheral surface of a support member (core member) with an aggregation of fibers (polyester fibers and/or polyamide fibers) (sheath material) for absorption and vaporization/diffusion of a liquid formulation. Materials for the thermal vaporization/diffusion absorbent wick will be described below.

After the measurement, measurement data is plotted on a graph where the vertical axis represents the rise distance (mm) and the horizontal axis represents the elapsed time (minute or hour), and a fitted straight line is drawn for each liquid formulation by least squares or the like. The slope of the fitted straight line for the water-based liquid formulation (i.e., the speed $(V_1)$ at which the water-based liquid formulation rises through the thermal vaporization/diffusion absorbent wick), and the slope of the fitted straight line for the oil-based liquid formulation (i.e., the speed ($V_2$) at which the oil-based liquid formulation rises through the thermal vaporization/diffusion absorbent wick), are calculated. The ratio ($V_1/V_2$) of these speeds is referred to as the "water/oil-based liquid absorption ratio" of the thermal vaporization/diffusion absorbent wick.

A feature of liquid mosquito killers is that a thermal vaporization/diffusion absorbent wick is put in a liquid formulation of an insecticidal composition, and the insecticidal composition is absorbed and transported to a top portion of the thermal vaporization/diffusion absorbent wick, where the insecticidal composition is heated at 60-130° C., so that a pyrethroid insecticidal component contained in the insecticidal composition is vaporized and diffused into the atmosphere, whereby insect pests are controlled. For an ideal water-based insecticidal composition (water-based liquid formulation) used in a liquid mosquito killer, when the thermal vaporization/diffusion absorbent wick is put in the water-based liquid formulation, the water-based liquid formulation rises through the thermal vaporization/diffusion absorbent wick while maintaining a balance between three components, i.e. an insecticidal component, a surfactant, and water, and is then vaporized and diffused from the top portion of the thermal vaporization/diffusion absorbent wick into the air. In fact, diethylene glycol monobutyl ether, which is the major component of the water-based liquid formulation, has a lower permeation rate through the thermal vaporization/diffusion absorbent wick than that of a fluid paraffin having 14 carbon atoms, which is the major component of the oil-based liquid formulation. Therefore, there is a difference in permeation rate between the components contained in the water-based liquid formulation, so that a component having a higher permeation rate may generally have a higher concentration at the top portion of the thermal vaporization/diffusion absorbent wick, and therefore, the composition fraction of that component may relatively increases. Such a phenomenon depends on properties of materials for the thermal vaporization/diffusion absorbent wick, the affinity between the thermal vaporization/diffusion absorbent wick and the liquid formulation, characteristics (vaporization and diffusion capability, viscosity, hydrophilicity, etc.) of each component, and the like, and particularly easily occurs for the water-based insecticidal composition.

This point has been further studied by the present inventors to find that when a water-based insecticidal composition containing a compound having a vapor pressure of $2 \times 10^{-4}$ to $1 \times 10^{-2}$ mmHg at 30° C. as the pyrethroid insecticidal component, and a glycol ether compound having a boiling point of 150-300° C., is used for thermal vaporization and diffusion, then if a thermal vaporization/diffusion absorbent wick having a water/oil-based liquid absorption ratio ($V_1/V_2$) defined above within the range of 0.55-1.0, preferably 0.60-0.85, is used, good vaporization and diffusion performance and practical insect killing efficacy are achieved. In other words, it has been clarified that an insect pest control product constructed by combining a water-based insecticidal composition satisfying the above range and a thermal vaporization/diffusion absorbent wick satisfying the above range can exploit full potential of the thermal vaporization/diffusion absorbent wick.

Incidentally, thermal vaporization/diffusion absorbent wicks for liquid mosquito killers are typically roughly divided into baked wicks, braided wicks, and bound wicks. In the present invention, baked wicks or braided wicks are preferably used. A case where a baked wick or a braided wick is used as the thermal vaporization/diffusion absorbent wick will be described. Note that any materials for the thermal vaporization/diffusion absorbent wick can be used that are stable with respect to the water-based insecticidal composition containing a pyrethroid insecticidal component, and can absorb aqueous solution through capillary action.

A baked wick is obtained by baking a mixture containing (a) an inorganic powder, (b) an inorganic binder, and (c) an organic substance, at 600-2000° C. A baked wick that contains only a small amount of the components (b) and (c), i.e. contains almost only an inorganic powder, may be referred to as a "ceramic wick."

Examples of the inorganic powder include mica, alumina, silica, talc, mullite, cordierite, zirconia, and the like. Of them, mica is preferable because it can impart relatively uniform fine pores to the thermal vaporization/diffusion absorbent wick. The above inorganic powders may be used alone or in combination. The content of the inorganic powder in the thermal vaporization/diffusion absorbent wick is preferably 10-90 mass %, more preferably 30-70 mass %. The inorganic powder is preferably fine powder of 50 mesh or finer in terms of physical properties such as external appearance, liquid absorption capability, strength, and the like, unless the process of manufacturing the thermal vaporization/diffusion absorbent wick is accompanied by pulverization.

Examples of the inorganic binder include clays such as kaolinite, bentonite, halloysite, and the like, tar pitch, water glass, and the like. Of them, clays are preferable because they have good binding capability. The above inorganic binders may be used alone or in combination. The content of the inorganic binder in the thermal vaporization/diffusion absorbent wick is preferably 5-50 mass %, more preferably 10-40 mass %. The inorganic binder has poor binding action at room temperature, and acquires sufficient binding action by being baked at 600-2000° C., so that it can be preferably used in the thermal vaporization/diffusion absorbent wick.

Examples of the organic substance include carbonaceous powders such as graphite, carbon black, activated carbon, charcoal, coke, and the like, or organic binders such as carboxymethyl cellulose (CMC), acrylic resins, polyolefin resins, and the like. Of them, graphite is preferably because it has a relatively uniform shape and contains less impurities. By adding a carbonaceous powder such as graphite or the like to the thermal vaporization/diffusion absorbent wick, the external appearance, color, liquid absorption capability, strength, and the like thereof can be improved. The above carbonaceous powders or organic binders may be used alone or in combination. The content of the organic substance in the thermal vaporization/diffusion absorbent wick is preferably 5-40 mass %. If the content is within this range, the generation of carbon monoxide or carbon dioxide during baking of the thermal vaporization/diffusion absorbent wick can produce continuous pores in the thermal vaporization/diffusion absorbent wick, so that a porous structure that can exert sufficient liquid absorption performance through capillary action is formed.

Note that, in addition to the above substances, the thermal vaporization/diffusion absorbent wick may additionally contain a preservative, and an antioxidant such as 4,4'-methylene bis(2-methyl-6-t-butylphenol), stearyl-β-(3,5-di-t-butyl-4-hydroxyphenyl)propionate, or the like, as appropriate.

A braided wick is typically obtained by covering the outer peripheral surface of a core member with a sheath material for absorbing and vaporizing/diffusing a water-based insecticidal composition, where the sheath material is formed as an aggregation of at least one fiber selected from natural fibers, synthetic fibers, and inorganic fibers. In braided wicks, the core member has the function of keeping the shape of the thermal vaporization/diffusion absorbent wick. The materials for the core member do not necessarily need to have the function of absorbing the water-based insecticidal composition. The core member may be made of, for example, a thermoplastic and/or thermosetting synthetic resin that can withstand temperatures of 130° C. or more. Note that, in order to enhance the shape retaining function, the thermoplastic and/or thermosetting synthetic resin of the core member may be reinforced using a fibrous reinforcing material such as glass fiber, ceramic fiber, carbon fiber, or the like, a powder reinforcing material such as silica, alumina, titanium oxide, or the like, which are called a glass powder or inorganic filler, or the like.

The sheath material is typically formed as an aggregation of fibers. The fiber includes one or more kinds of fibers. Examples of the fibers include natural fibers such as cotton and the like, synthetic fibers such as polypropylene, polyester, polyamide, nylon, aramid, and the like, inorganic fibers such as glass fiber, carbon fiber, and the like. Synthetic fibers that can withstand temperatures of 130° C. or more, such as polypropylene, polyester, nylon, aramid, and the like, are preferable. Such a fiber aggregation is typically made of a fiber material in the form of braid, woven fabric, knitted fabric, felt, or nonwoven fabric. In this case, the fiber material may be treated with a surfactant so that the liquid absorption speed is adjusted. Furthermore, the surface of the sheath material may be covered with a varnish or the like, or may be treated so that a function such as hydrophilicity or the like is imparted thereto.

The thermal vaporization/diffusion absorbent wick thus obtained is applied to the insect pest control product (water-based liquid mosquito killer) of the present invention, in which the water-based insecticidal composition is thermally vaporized and diffused through the thermal vaporization/diffusion absorbent wick. Specifically, the water-based insecticidal composition is accommodated in a chemical liquid container made of a plastic such as polypropylene, polyester, polyvinyl chloride, or the like. The thermal vaporization/diffusion absorbent wick is put into the water-based insecticidal composition through a stopper. Thereafter, the water-based insecticidal composition in the container is transported to the top portion of the absorbent wick, and is heated to 60-130° C. by a ring-shaped heat generator provided around the top portion to be vaporized and diffused into the atmosphere. The thermal vaporization/diffusion absorbent wick faces the heat generator with a space therebetween. Therefore, the desired surface temperature (e.g., 60-130° C.) of the top portion of the absorbent wick is achieved by adjusting the heat generator to a higher temperature (e.g., 80-150° C.). If the heating temperature of the water-based insecticidal composition is excessively high, the water-based insecticidal composition is likely to be quickly vaporized and diffused, or the water-based insecticidal composition is likely to undergo pyrolysis or polymerization, leading to the production of a high-boiling-point substance on the surface of the thermal vaporization/diffusion absorbent wick, which may be accumulated to clog the absorbent wick. Meanwhile, if the heating temperature is excessively low, the water-based insecticidal composition has difficulty in vaporizing and diffusing, so that sufficient insect control performance cannot be achieved.

The insect pest control product of the present invention may be provided with various functions and members similar to those of conventional devices in addition to the above heat generator. For safety, a protective cap is provided over the heat generator. The protective cap has an opening at a center portion thereof. The size and shape of the opening may be arbitrarily determined as long as the liquid formulation vaporized and diffused does not excessively condense or adhere to the protective cap or the device. For example, to provide a cylindrical vaporization/diffusion tube having an inner diameter of 10-30 mm, hanging vertically from near the opening, is effective. In this case, the distance between the lower end of the vaporization/diffusion tube and the top surface of the heat generator is preferably typically within the range of 1-5 mm in terms of the heat resistance and vaporization/diffusion performance of the vaporization/diffusion tube. The insect pest control product of the present invention may be additionally provided, as appropriate, with a power supply cord, on-off operation switch, pilot light, etc., which are connected to the heat generator.

The insect pest control method of using the insect pest control product of the present invention has practical insect killing efficacy, in indoor spaces such as living rooms, lounges, bedrooms, and the like, on not only strains that are susceptible to pyrethroids, but also strains that have reduced susceptibility, of mosquitoes such as Culex (Culex pipiens pallens, Culex tritaeniorhynchus, Culex pipiens quinquefasciatus, Culex pipiens molestus, etc.), Aedes (Aedes aegypti, Aedes albopictus, etc.), Chironomidae, and the like, and other flying insect pests such as houseflies, drain flies, phorid flies, horseflies, black flies, biting midges, and the like, and therefore, is considerably useful. The insect pest control method is also similarly effective in controlling creeping insect pests such as cockroaches, fleas, and bedbugs.

EXAMPLES

Next, the insect pest control product and insect pest control method of the present invention will be described in greater detail by way of specific examples.

Example 1

A water-based insecticidal composition was prepared by mixing 0.9 mass % of transfluthrin, 50 mass % of diethylene glycol monobutyl ether (DEMB), 0.1 mass % of dibutylhydroxytoluene (BHT) as a stabilizer, and 49 mass % of purified water.

A thermal vaporization/diffusion absorbent wick (a round bar having a diameter of 7 mm and a length of 66 mm) was obtained as follows: water was added to a mixture of 55 mass % of mica powder as the inorganic powder, 30 mass % of clay powder as the inorganic binder, 10 mass % of graphite as the organic substance, 3 mass % of carboxymethyl cellulose as the organic binder, and 2 mass % of starch, followed by kneading, the kneaded mixture was extruded while pressure was applied thereto, followed by air drying and then baking at 1000° C. The thermal vaporization/diffusion absorbent wick had a water/oil-based liquid absorption ratio of 0.63.

Forty-five milliliters of the water-based insecticidal composition was placed in a plastic container, and the thermal vaporization/diffusion absorbent wick was loaded into the container through the stopper. The container was attached to a thermal vaporization/diffusion device (e.g., a device disclosed in Japanese Patent No. 2926172 or the like, and the temperature of a ring-shaped heat generator disposed around the top portion of the absorbent wick was adjusted to 130° C.) Thus, the insect pest control product (water-based liquid mosquito killer) was constructed. The insect pest control product was placed at the center of a room having an area of 6 Jyos (Jyo is a Japanese unit of area: 1 Jyo is equal to approximately 1.7 m$^2$) (25 m$^3$), and was used while an electric current was passed through the heat generator for 12 hours per day. For 60 days (approximately 700 hours), no mosquito biting was observed.

Examples 2-10 and Comparative Examples 1-6

Water-based insecticidal compositions and thermal vaporization/diffusion absorbent wicks according to Examples 2-10 were prepared in a manner similar to that for Example 1, and were loaded into respective thermal vaporization/diffusion devices to construct respective insect pest control products, which were tested to verify their efficacy. For comparison, insect pest control products using water-based insecticidal compositions and thermal vaporization/diffusion absorbent wicks according to Comparative Examples 1-6 were similarly tested to verify their efficacy. The components of the water-based insecticidal compositions and the thermal vaporization/diffusion absorbent wicks of the examples and the comparative examples are shown in Table 1.

TABLE 1

|  |  | Water-based insecticidal composition (mass %) | | | Thermal vaporization/diffusion absorbent | | Water/oil-based liquid absorption ratio (V1/V2) |
|---|---|---|---|---|---|---|---|
|  |  | Insecticidal components | Glycol ether compounds | Other components excluding water | Type | Major components (mass %) |  |
| Examples | 1 | Transfluthrin 0.9 | DEMB 50 | BHT 0.1 | Baked | Mica powder 55 Clay powder 30 Graphite 10, etc. | 0.63 |
|  | 2 | Metofluthrin 0.5 | DEMB 50 | BHT 0.1 | Baked | Mica powder 40 Bentonite 35 Coke 15, etc | 0.61 |
|  | 3 | Transfluthrin 0.9 | DEMB 50 | BHT 0.1 | Baked | Mica powder 55 Clay powder 30 Graphite 10, etc. | 0.92 |
|  | 4 | Transfluthrin 0.9 | DEMIB 50 | BHT 0.1 | Braided | Polyester/ polyamide | 0.70 |
|  | 5 | Transfluthrin 0.9 | DEMIB 50 | BHT 0.1 | Braided | Polyester/ polypropylene | 0.58 |
|  | 6 | Transfluthrin 0.9 | DEMIB 50 | BHT 0.1 | Braided | Polyester/ polyamide | 0.89 |
|  | 7 | Metofluthrin 0.5 | DEMB 50 | BHT 0.1 | Braided | Polyester/ polyamide | 0.72 |
|  | 8 | Profluthrin 0.8 Metofluthrin 0.2 | DPMP 70 | Tea leaf dry distilled solution 0.1 | Baked Ceramic | Mullite, etc. | 0.77 |
|  | 9 | Transfluthrin 0.9 | DEMIP 50 | BHT 0.1 Aroma chemical Small amount | Baked | Talc powder 41 Clay powder 36 Acrylic resin 10, etc. | 0.56 |
|  | 10 | Empenthrin 2.0 | DEMB 50 | BHT 0.1 | Braided | Polyester/ polyamide | 0.79 |
| Comparative Examples | 1 | Transfluthrin 0.9 | DEMB 50 | BHT 0.1 | Baked | Mica powder 55 Clay powder 30 Graphite 10, etc. | 0.47 |
|  | 2 | Metofluthrin 0.5 | DEMB 50 | BHT 0.1 | Braided | Polyester/ polyamide | 0.51 |
|  | 3 | Metofluthrin 0.5 | Glycol ether A* 70 | BHT 0.1 | Braided | Polyester/ polyamide | 0.93 |
|  | 4 | Transfluthrin 0.9 | Glycol ether B** 50 | BHT 0.1 | Baked | Mica powder 55 Clay powder 30 Graphite 10, etc. | 0.59 |
|  | 5 | dl•d-T80-allethrin 2.0 | DEMB 50 | BHT 0.1 | Baked | Mica powder 55 Clay powder 30 Graphite 10, etc. | 0.62 |
|  | 6 | dl•d-T80-allethrin 2.0 | DEMB 50 | BHT 0.1 | Baked | Mica powder 30 Clay powder 40 Graphite 25, etc. | 0.50 |

*Glycol ether A: ethylene glycol monomethyl ether (boiling point: 124° C.)
**Glycol ether B: diethylene glycol monobenzyl ether (boiling point: 302° C.)

<Vaporization and Diffusion Performance>

An insect pest control product to be tested was placed at the center of a 6-Jyo room (25 m$^3$), and fumigation was performed by heating the thermal vaporization/diffusion absorbent wick through the passage of an electric current. The insecticidal component was trapped using a silica gel-filled column, extracted using acetone, and analyzed by gas chromatography, at predetermined time intervals, so that the amount of the insecticidal component vaporized and diffused per unit time was calculated.

<Efficacy Verification Test>

Two plastic cylinders each having an inner diameter of 20 cm and a height of 43 cm were put on top of each other. Another cylinder having an inner diameter of 20 cm and a height of 20 cm (insects to be tested were to be placed), which is vertically partitioned by a 16-mesh metal mesh, was put on top of the stack of the two cylinders with a rubber gasket being interposed therebetween. Still another cylinder having the same inner diameter and a height of 20 cm was put on top of the third cylinder. The stack of the four cylinders was placed on a circular plate provided on a table with a rubber gasket being interposed between the cylinder stack and the circular plate. The circular plate had a 5-cm circular hole at the center thereof. An insect pest control product was placed on the circular hole, and fumigation was performed by heating the thermal vaporization/diffusion absorbent wick through the passage of an electric current. After four hours of the passage of an electric current, approximately 20 adult female Culex pipiens pallens mosquitoes (insects to be tested) were released in the upper cylinder, and the number of tested insects which fell down to be flat on their back as time passed was counted to calculate the $KT_{50}$ value. After 20 minutes of exposure, all of the tested insects were collected. The fatality rate of the insects was investigated 24 hours later.

The test results of the examples and the comparative examples are shown in Table 2.

nent vaporized and diffused tended to be initially great, and thereafter, significantly decrease. Therefore, a sufficient insect killing efficacy to achieve the object of the present invention was not obtained. Furthermore, in Comparative Examples 3 and 4, in which the boiling point of the glycol ether compound does not fall within the predetermined range, and in Comparative Examples 5 and 6, in which the vapor pressure of the pyrethroid insecticidal component does not fall within the predetermined range, the thermal vaporization/diffusion absorbent wicks did not have effective vaporization and diffusion performance or insect killing efficacy, even if their water/oil-based liquid absorption ratios ($V_1/V_2$) fell within the predetermined range.

INDUSTRIAL APPLICABILITY

The insect pest control product and insect pest control method of the present invention can be used to protect

TABLE 2

| | | Vaporization and diffusion performance (mg/h) | | | Insect killing efficacy test | | | |
|---|---|---|---|---|---|---|---|---|
| | | | | | Early part of period of use | | Late part of period of use | |
| | | Early part of period of use | Middle part of period of use | Late part of period of use | $KT_{50}$ (sec) | Fatality rate (%) | $KT_{50}$ (sec) | Fatality rate (%) |
| Examples | 1 | 0.56 | 0.54 | 0.49 | 108 | 100 | 120 | 100 |
| | 2 | 0.33 | 0.30 | 0.27 | 103 | 100 | 116 | 100 |
| | 3 | 0.48 | 0.45 | 0.43 | 117 | 100 | 141 | 100 |
| | 4 | 0.54 | 0.51 | 0.48 | 104 | 100 | 125 | 100 |
| | 5 | 0.68 | 0.59 | 0.41 | 98 | 100 | 147 | 100 |
| | 6 | 0.47 | 0.43 | 0.42 | 115 | 100 | 142 | 100 |
| | 7 | 0.31 | 0.28 | 0.25 | 110 | 100 | 126 | 100 |
| | 8 | (Profluthrin) 0.52 (Metofluthrin) 0.13 | 0.48 0.11 | 0.43 0.09 | 121 | 100 | 137 | 100 |
| | 9 | 0.71 | 0.53 | 0.45 | 95 | 100 | 145 | 100 |
| | 10 | 1.39 | 1.05 | 0.86 | 122 | 100 | 143 | 90 |
| Comparative Examples | 1 | 0.94 | 0.39 | 0.20 | 89 | 100 | 208 | 45 |
| | 2 | 0.55 | 0.28 | 0.11 | 83 | 100 | 197 | 65 |
| | 3 | 0.41 | 0.27 | 0.12 | 94 | 100 | 191 | 60 |
| | 4 | 0.35 | 0.28 | 0.21 | 170 | 70 | 204 | 50 |
| | 5 | 0.72 | 0.49 | 0.34 | 248 | 40 | 316 | 25 |
| | 6 | 1.46 | 1.29 | 1.03 | 185 | 75 | 267 | 45 |

The thermal vaporization/diffusion absorbent wicks of Examples 1-10 were applied to a water-based insecticidal composition containing a pyrethroid insecticidal component having a vapor pressure of $2\times10^{-4}$ to $1\times10^{-2}$ mmHg at 30° C., a glycol ether compound having a boiling point of 150-300° C., and water. According to the test results, it was verified that the thermal vaporization/diffusion absorbent wicks have a water/oil-based liquid absorption ratio ($V_1/V_2$) within the range of 0.55-1.0, and therefore, have stable vaporization and diffusion performance and good insect killing efficacy no matter whether they are a baked wick or a braided wick, and are considerably effective in controlling flying insect pests, particularly mosquitoes. In particular, in Examples 1-9, in which transfluthrin, metofluthrin, and/or profluthrin are contained as the pyrethroid insecticidal component, a fatality rate of 100% was achieved from early to late parts of the period of use.

In contrast to this, in Comparative Examples 1 and 2, although a predetermined pyrethroid insecticidal component and glycol ether compound were used, the water/oil-based liquid absorption ratios ($V_1/V_2$) of the thermal vaporization/ diffusion absorbent wicks did not fall within the range of 0.55-1.0. As a result, the amount of the insecticidal compohumans and pets from insect pests, and can also be used for other purposes, such as insecticidal, acaricidal, antibacterial, antifungal, deodorizing, and antibromic applications.

The invention claimed is:

1. An insect pest control product comprising a thermal vaporization/diffusion absorbent wick for vaporizing and diffusing a water-based insecticidal composition containing a pyrethroid insecticidal component having a vapor pressure of $2\times10^{-4}$ to $1\times10^{-2}$ mmHg at 30° C., a glycol ether compound having a boiling point of 150-300° C., and water, wherein
    the thermal vaporization/diffusion absorbent wick has a water/oil-based liquid absorption ratio ($V_1/V_2$) within the range of 0.55-1.0,
    where the water/oil-based liquid absorption ratio ($V_1/V_2$) is calculated from a speed ($V_1$) at which a water-based liquid formulation rises through the thermal vaporization/diffusion absorbent wick when a lower portion of the thermal vaporization/diffusion absorbent wick is immersed in the water-based liquid formulation, and a speed ($V_2$) at which an oil-based liquid formulation rises through the thermal vaporization/diffusion absorbent wick when a lower portion of the thermal vaporization/diffusion absorbent wick is immersed in the oil-based liquid formulation, where the water-based liquid formulation is an aqueous solution containing 40 mass % of diethylene glycol monobutyl ether, and the oil-based liquid formulation is a fluid paraffin having 14 carbon atoms.

2. The insect pest control product of claim 1, wherein the water/oil-based liquid absorption ratio ($V_1/V_2$) is within the range of 0.60-0.85.

3. The insect pest control product of claim 1, wherein the pyrethroid insecticidal component is at least one selected from the group consisting of transfluthrin, metofluthrin, and profluthrin.

4. The insect pest control product of claim 1, wherein the thermal vaporization/diffusion absorbent wick is a baked wick or a braided wick.

5. The insect pest control product of claim 4, wherein the baked wick contains, as raw materials, an inorganic powder, an inorganic binder, and an organic substance.

6. The insect pest control product of claim 4, wherein the braided wick has a core member, and a sheath material covering an outer peripheral surface of the core member, and
the sheath material contains at least one fiber selected from the group consisting of natural fibers, synthetic fibers, and inorganic fibers.

7. An insect pest control method of using the insect pest control product of claim 1, comprising:
putting the thermal vaporization/diffusion absorbent wick in the water-based insecticidal composition so that the water-based insecticidal composition is absorbed and transported to a top portion of the thermal vaporization/diffusion absorbent wick, and heating the top portion at 60-130° C. so that the pyrethroid insecticidal component is vaporized and diffused into the atmosphere.

8. The insect pest control product of claim 2, wherein the pyrethroid insecticidal component is at least one selected from the group consisting of transfluthrin, metofluthrin, and profluthrin.

9. The insect pest control product of claim 2, wherein the thermal vaporization/diffusion absorbent wick is a baked wick or a braided wick.

10. The insect pest control product of claim 3, wherein the thermal vaporization/diffusion absorbent wick is a baked wick or a braided wick.

11. The insect pest control product of claim 8, wherein the thermal vaporization/diffusion absorbent wick is a baked wick or a braided wick.

12. The insect pest control product of claim 9, wherein the baked wick contains, as raw materials, an inorganic powder, an inorganic binder, and an organic substance.

13. The insect pest control product of claim 10, wherein the baked wick contains, as raw materials, an inorganic powder, an inorganic binder, and an organic substance.

14. The insect pest control product of claim 11, wherein the baked wick contains, as raw materials, an inorganic powder, an inorganic binder, and an organic substance.

15. The insect pest control product of claim 9, wherein the braided wick has a core member, and a sheath material covering an outer peripheral surface of the core member, and
the sheath material contains at least one fiber selected from the group consisting of natural fibers, synthetic fibers, and inorganic fibers.

16. The insect pest control product of claim 10, wherein the braided wick has a core member, and a sheath material covering an outer peripheral surface of the core member, and
the sheath material contains at least one fiber selected from the group consisting of natural fibers, synthetic fibers, and inorganic fibers.

17. The insect pest control product of claim 11, wherein the braided wick has a core member, and a sheath material covering an outer peripheral surface of the core member, and
the sheath material contains at least one fiber selected from the group consisting of natural fibers, synthetic fibers, and inorganic fibers.

* * * * *